United States Patent [19]

Meyer et al.

[11] Patent Number: 4,809,711

[45] Date of Patent: Mar. 7, 1989

[54] PREFILLED AMPOULE-SYRINGE

[75] Inventors: Gabriel Meyer; Ernst Howald, both of Vesenaz, Switzerland

[73] Assignee: Medicorp Holding S.A., Luxembourg, Luxembourg

[21] Appl. No.: 927,829

[22] Filed: Nov. 6, 1986

Related U.S. Application Data

[63] Continuation-in-part of Ser. No. 561,057, Dec. 13, 1983, abandoned.

[30] Foreign Application Priority Data

Dec. 20, 1982 [CH] Switzerland ........................ 82/00134

[51] Int. Cl.[4] ................................................ A61B 5/00

[52] U.S. Cl. ...................................... 128/766; 604/236

[58] Field of Search .......... 604/89, 203, 231, 236–238; 128/764–766

[56] References Cited

U.S. PATENT DOCUMENTS

| | | | |
|---|---|---|---|
| 1,139,720 | 5/1915 | Reed | 604/326 |
| 2,893,390 | 7/1959 | Lockhart | 604/238 |
| 3,464,412 | 9/1969 | Schwartz | 604/89 |
| 4,479,801 | 10/1984 | Cohen | 604/238 |

*Primary Examiner*—C. Fred Rosenbaum

*Assistant Examiner*—J. Kruter

*Attorney, Agent, or Firm*—Hayes, Davis & Soloway

[57] ABSTRACT

A prefilled ampoule-syringe comprising an ampoule and an ampoule body having a single open end and a neck located near the single open end, the neck having a smaller transverse inner dimension then said body. A stopper, associated with an external capsule, has an internal conduit to allow communication between the interior of the ampoule body and the injection tip, the stopper being arranged for axial movement within said neck from a closed to an open position. An upper part of the stopper having at least one continuous annulus surface having a larger outer dimension than the inner dimension of the ampoule neck so as to be in a sealing compressed condition in the closed position and having a smaller outer dimension than the inner dimension of the ampoule body so as to be in a partly expanded condition in said open position to permit the flow of liquid from the ampoule body to the tip. The lower part of the stopper has at least one continuous annulus surface to prevent the flow of any liquid past the lower portion of the stopper in both the closed and opened positions. The length of the rod element is equal to at least the axial length of the ampoule body and neck.

7 Claims, 2 Drawing Sheets

PREFILLED AMPOULE-SYRINGE

This is a continuation-in-part of 06/561,057 filed 12/13/83 now abandoned.

The present invention relates to a prefilled ampoule-syringe containing a liquid medication and a gas.

BACKGROUND OF THE INVENTION

Syringe-ampoules are already known in the art, particularly those described in French Pat. No. 714108. These devices are comprised of an ampoule provided with a stopper encased by the open end of the ampoule, and associated with a rotatable valve traversed by an axial conduit, connected to a radial conduit designed to open into a cavity in communication with the interior of the ampoule. In the example illustrated in FIGS. 1 and 2 of this patent, the opening and closing of the valve are affected by the rotation of the needle carrier. The solution is not useful in practice, since the operator has only one hand available to hold the syringe and to activate the valve, his other hand being occupied holding the patient's skin.

The embodiment of FIG. 3 of this patent demonstrates one solution to this problem. However, the manufacture of the ampoule-syringe described is very costly and the product unsatisfactory in numerous respects. Actually, this construction entails a stopper which is in contact with the pharmaceutical substance or liquid medication contained in the ampoule, a rotatable valve contained in a central opening disposed in the stopper means and also in partial contact with the substance to be injected, a special needle-holding cap adapted to the stopper means and a spiral spring between the stopper and the cap.

The manufacture of a special needle and needle holder is a costly operation. The fact that the needle is mounted on a needle-holding tip at the time of assembly and especially at the time the ampoule is pressurized means that the pressurized gas to be introduced into the ampoule must be injected through the syringe, thereby necessitating a complicated mechanism to avoid damaging the needle. This could also be achieved by filling the ampoule in a pressurized room or container, but the operation is complicated and relatively costly. The pressurization of the pharmaceutical substance could be accomplished by injecting the gas through the needle holding tip, previously positioned, followed by soldering or gluing the needle. Manipulating the needle is costly because it necessitates the utmost precautions. It must be done under sterile conditions to exclude any contamination, particularly glue residue.

The pharmaceutical substance is in contact with three elements made of different materials, the ampoule, the stopper and the valve. Furthermore, water-tightness between the stopper and the valve is difficult to achieve unless the body of the valve is firmly attached to the interior of the stopper, thereby causing considerable pull which impedes retraction of the ampoule at the time of injection.

Maintaining the stopper in place necessitates use of an encasing ring. The elements comprising the stopper means for the ampoule are the following: a stopper, a valve situated in a cylindrical cavity of said stopper, an encasing ring, a needle holding cap, a spring and a needle. Manufacturing and assembling all these pieces is extremely costly. Furthermore, preparation of the syringe for use requires the following operations: filling the ampoule with the pharmaceutical substance, placing the stopper on the ampoule, affixing the stopper by means of the encasing ring, positioning the valve in the central opening of the stopper, positioning the spring, injecting compressed gas into the ampoule to pressurize the liquid and affixing the needle. These various preparatory phases are both delicate and costly. Further this kind of syringe does not permit aspiration of liquid, i.e. for checking presence of blood for intravenous injections or absence of blood for subcutaneous or intramuscular injections. Furthermore, it is known from the article which appears on page 17 of "Recipients en matiere plastique pour les preparations pharmaceutiques, essai et controle" ("Plastic Containers for Pharmaceuticals Preparations, Experimentations and Control"), published in 1974 by the World Health Organization, and authored by Jack Cooper, that composite containers are often susceptible to interaction of materials. In particular, there has been observed a migration of certain components of synthetic material into pharmaceutical substance contents. Interaction between the pharmaceutical substance contents and the container when the latter is made of a polymer may change the physical characteristics of the polymer and/or pharmacological characteristics of the pharmaceutical substance contents. Even if its characteristics are initially satisfactory, the changes which may occur as a result of the prolonged interaction oblige manufacturers to pay particular attention to stability during storage.

Many other prefilled ampoule-syringes are known, comprising an ampoule containing liquid medication under pressure and a stopper means which closes the ampoule until it is used. One document which particularly well illustrates a technique currently in use is British Pat. No. 13142 which describes a prefilled ampoule-syring stoppered by a water-airtight stopper designed to be pierced by a double needle, one end of which penetrates through the stopper to the interior of the ampoule and the other end of which is for injecting the pharmaceutical substance into the patient's body. Pressurization of such ampoule must take place automatically in a pressurized atmosphere because the stopper is effective in one direction only. The needle, which has a specialized shape, requires a special and relatively costly manufacturing process, as a standard needle cannot be used with this device. Finally, piercing an elastomer stopper with a double needle can cause migration of inert particles into the pharmaceutical substance and into the patient's body, thereby posing a real danger to the patient.

A fluid withdrawal device and container disclosed in U.S. Pat. No. 3,159,159 which can also be used as a prefilled syringe, comprises a valve system for dispensing a liquid medication which is maintained under pressure in an adequate ampoule. The valve system functions like a stopper during a storage phase and like a spring actuated valve during the injection phase. The construction is complicated and the liquid is in contact with at least three different materials. Like the French patent, this device does not allow aspiration where it is used as a prefilled syringe.

A fluid dispensing device disclosed in U.S. Pat. No. 4,479,801 comprises a syringe body having a first opening which can be closed by an axially movable stopper and a separate piston for pushing the liquid through the movable stopper to an injection needle. The movable stopper functions like a valve for closing a passageway during the storage phase and for opening the same during the injection phase. The ampoule has two openings and the liquid is in contact with at least three different materials. The present invention proposes to overcome the various foregoing disadvantages and to offer the health profession a useful instrument, easy to manipulate, of economical construction and providing the patient with the requisite hygiene and cleanliness.

SUMMARY OF THE INVENTION

The main object of the present invention is a prefilled ampoule-syringe of the above type comprising an ampoule with an ampoule body having a single open end and a neck located near the single open end, this neck having smaller transverse inner dimensions than said body, and a stopper means associated with an external capsule, said stopper means being provided with an internal conduit having at least one transverse branch opening into a longitudinal branch for communications of the interior of the ampoule body with an injection device holding tip, said stopper means being arranged for axial movement within said neck in a closed storage position and within said ampoule body in an open injection/aspiration position; in which said stopper means comprises a stopper body made of resilient material and having an upper part located above said transverse branch and a lower part located below said transverse branch, and a rod element for attaching solidly at least said lower part of said stopper body to said external capsule, in which said upper part of said stopper body is provided with at least one continuous annular surface having larger transverse outer dimensions than the transverse inner dimensions of said ampoule neck so as to be in a compressed condition in said closed storage position, being sealingly engaged in direct contact with the inner wall of said neck in said closed storage position so as to prevent flow of liquid from the ampoule body to said transverse branch, and having at least partly smaller transverse outer dimensions than the transverse inner dimensions of said ampoule body, so as to be in at least a partly expanded condition in said open injection/aspiration position, and being at least partly disengaged from the inner wall of said ampoule body in said open injection/aspiration position, so as to permit flow of liquid from the ampoule body to said transverse branch, in which said lower part of said stopper body is provided with at least one continuous annular surface having larger transverse outer dimensions than the transverse inner dimensions of said ampoule neck so as to be in a compressed condition in said closed storage position and being sealingly engaged in direct contact with said inner wall of said neck in said closed position, and having also larger outer dimensions than the transverse inner dimensions of said ampoule body so as to remain in at least a partly compressed condition in said open injection/aspiration position, and being sealingly engaged in direct contact with the inner wall of said ampoule body in said open injection/aspiration position so as to prevent accidental flow of liquid from the transverse branch to the open end of the ampoule body, and in which the total length of the stopper means from the upper end of the upper part of said stopper body to the zone where the rod element is attached to the external capsule is at least equal to the total axial length of said ampoule body and said neck.

According to a preferred embodiment of the invention said upper part and said lower part of said stopper body are integral.

According to another preferred embodiment, said upper part and said lower part of said stopper body are separate elements.

Said lower part of said stopper body can be integral with said rod element.

Advantageously, said continuous annular surface of said upper part of said stopper body is provided with at least one ring-shaped rim and said continuous annular surface of said lower part of said stopper body is provided with at least one ring-shaped rim or at least one ring-shaped strip or tongue.

BRIEF DESCRIPTION OF THE DRAWINGS

The present invention, its characteristics and principal advantages will be better understood with reference to the description of embodiments thereof and to the attached drawings in which.

DESCRIPTION OF THE PREFERRED EMBODIMENTS

Figure 1:
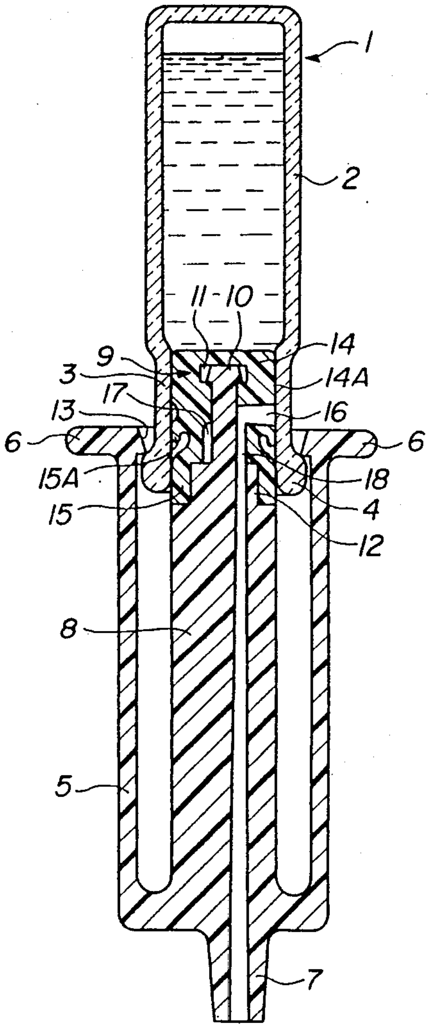
FIG. 1 is an axial section of an preferred embodiment of the prefilled ampoule-syringe of the invention, in which the stopper means is in the closed storage position.
Figure 2:
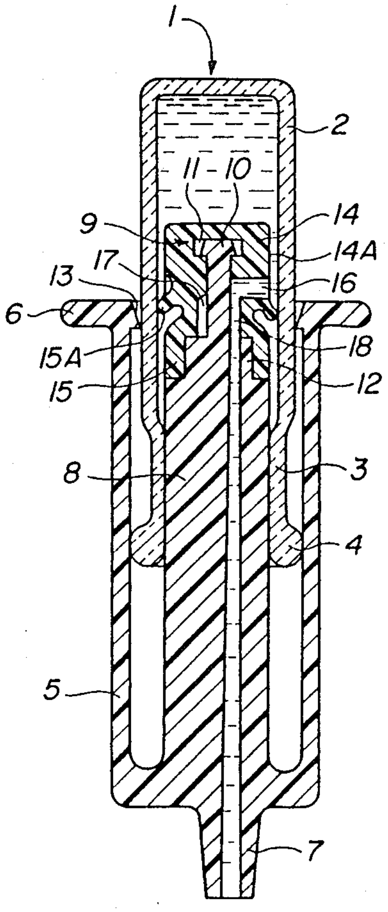
FIG. 2 is a similar view in which the stopper means is in the injection position.

The prefilled ampoule-syringe according to FIGS. 1 and 2 comprises an ampoule 1 provided with an ampoule body 2 and a neck 3 of smaller transverse inner dimensions than said body. In a preferred embodiment the ampoule body and the neck have both a cylindrical shape and both inner and outer transverse dimensions of the neck are smaller than the outer diameter of said ampoule body. Neck 3 is provided with an opening which is preferably the only opening of the ampoule. For some special applications the ampoule body 2 could be provided with a fixed stopper located at its end opposed to the neck. Neck 3 is further provided with a peripheral rim 4 having preferably transverse outer dimensions equal to the outer diameter of the ampoule body 2. A great number of such ampoules 1 can therefore be positioned side-by-side and transferred on a transfer unit, such as i.e. an endless conveyor, to and away from an automatic filling up station.

An external capsule 5 is adapted to the neck 3 of ampoule 1. External capsule 5 is made of a relatively rigid plastic material and is provided with at least two diametrically opposed projections 6 forming two finger grips and with a conical injection device holder tip 7. In the embodiments of FIGS. 1 and 2, the needle holder tip is not centered. Such an asymmetric embodiment is particularly useful when injecting a large volume of medication. But it is understood that in other embodiments the needle holder tip can be centered on the axis of the ampoule-syringe.

In this case, external capsule 5 is integral with a rod element 8 also made of the same relatively rigid plastic material as the capsule 5. A stopper body 9 is mounted on the free end of the rod element 8. Rod element 8 is therefore provided, at its free end with a tip 10 having a T-shape which engages into a complementary shaped cavity 11 located inside the stopper body 9. A tapered part 12 is located between the T-shaped tip 10 and the body of the rod element 8.

An open circular end of the capsule 5 is provided with a protruding rim 13 having inner diameter less than the outer diameter of the rim 4 of neck 3. This protruding rim 13 is provided for cooperating with said rim 4 to ensure that capsule 5 is retained on ampoule 1 when the stopper means is in its storage position. The protruding rim 13 may also be replaced by discontinuous protruding members.

Stopper means comprises said stopper body 9 and said rod element 8. Stopper body 9 comprises an upper part 14 extending around the T-shaped tip of the rod element 8 and a lower part 15 extending around the tapered part 12 of rod element 8. Stopper means is further provided with an internal conduit having at least one transverse branch 16 communicating, directly or through a central cavity 17 with a longitudinal branch 18 provided through said rod element 8. Longitudinal branch 18 can be axial or parallel to the axis of stopper body 9. It is preferably located on the same line and communicates directly with a passageway 19 provided axially through injection device tip holder. The upper part 14 of the stopper body 9 is located above said transverse branch 16 and the lower part 15 of the stopper body 9 is located below said transverse branch 16.

In the embodiment represented by FIGS. 1 and 2, the stopper body 9 is provided with only one transverse branch 16. In other embodiments the transverse branch 16 could comprise two or more radial passageways.

Along its periphery, the upper part 14 of the stopper body 9 is provided with at least one continuous annular surface, 14A which is sealingly engaged in direct contact with the inner wall of the neck 3 in the closed storage position represented by FIG. 1. This surface 14A can be the whole peripheral surface of said upper part 14 or it can also be provided by one or more annular rims. In said closed storage position, this continuous annular surface is in a compressed condition and prevents any accidental passage of liquid from the ampoule body to the transverse branch 16.

Along its periphery, the lower part 15 of the stopper body 9 is provided with at least one continuous annular surface 15A which is sealingly engaged in direct contact with the inner wall of the neck 3 in the closed storage position represented by FIG. 1. In the embodiment represented by FIGS. 1 and 2, this annular surface has the shape of an annular strip or tongue which is in a compressed condition in said closed storage position.

In the open injection/aspiration position, the continuous annular surface 14A is in a expanded position and, as represented by FIG. 2, is disengaged from the inner wall of the ampoule body. For this reason, the liquid contained in the ampoule body is allowed to flow between the surface 14A and the ampoule body inner wall to the transverse branch 16. In this position, the continuous annular surface 15A of the lower part 15 of the stopper body 9 is also in a partly expanded condition, but it remains sealingly in direct contact with the inner wall of the ampoule body. For this reason, the liquid contained in the ampoule body is not allowed to flow between said surface 15A and the inner wall of the ampoule body, therefore preventing an accidental leakage of the liquid to the open end of the neck 3. The continuous annular surface 15A, being sealingly in contact with the inner wall of the ampoule body acts as a piston segment and forces the liquid into the transverse branch 16.

In the storage position represented by FIG. 1, the liquid medication is never in contact with anything other than the material forming the upper part 14 of the stopper body 9 and with the glass or plastic wall of the ampoule body. This material is an elastomer or any other appropriate material with elastic characteristics. The impermeability of the ampoule between the rigid wall of the ampoule neck and the annular surface 14A of said upper part 14 is perfectly assured.

In FIG. 2 shows the injection phase of the syringe according to the invention. In practice, the gas contained in the ampoule 1 is preferably released before the injection of the liquid medication. To this end, the syringe is to be returned so that the injection device, i.e. a needle (not shown) which is adapted on the injection device holder tip 7 is directed upwardly. The ampoule 1 is then pushed partially into the capsule 5.

During the first step, the upper part 14 of the stopper body 9 penetrates into the ampoule body. This introduction of the stopper means into the ampoule body provides a reduction of the effective volume of the ampoule, and induces an increase in the pressure of the gas contained in this ampoule since the liquid medication is incompressible. The first step extends to the point when the continuous annular surface 14A of the upper part 14 of the stopper body 9 is completely inside the ampoule body. At this moment the gas under pressure partially escapes.

This is the beginning of the second step. The end of this second step occurs when all the gas is evacuated. In practice this happens when the upper face of the upper part 14 enters into contact with the liquid medication, and when a first drop of this liquid appears at the distal end of the needle.

Preliminary releasing of gas is not a necessary phase. The gas remainded after injection of the liquid medication can be used to evacuate the last drops of liquid out of the internal conduit and of the needle so as to eliminate any dead volume of remaining liquid.

At this moment, the syringe is ready for the injection. The third step is the injection phase. As described above both during the second and third steps, the annular surface 15A having the shape of a strip or tongue which was in a compressed condition during the first step is now partially released and performs the function of a piston segment which maintains the tightness between the walls of the ampoule body and the lower part of said stopper body. The liquid medication is forced to penetrate into the transverse branch 16 and to flow through the axial branch 18 in direction of the needle holder tip 7.

Figure 3:
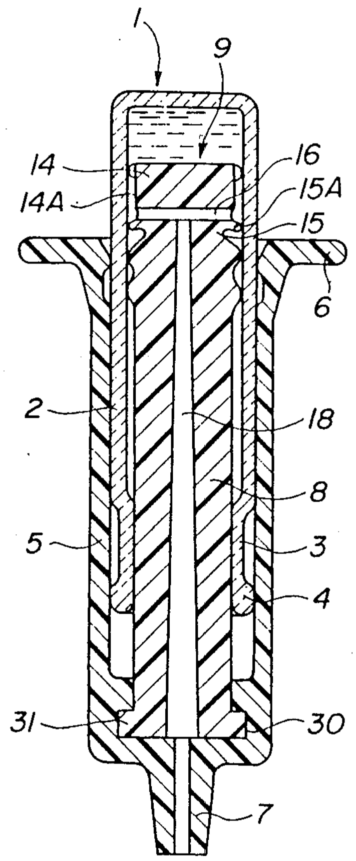
FIG. 3 is an axial section of another embodiment of the prefilled ampoule-syringe of the invention, in which the stopper means is in the injection position.

FIG. 3 shows another embodiment of the syringe according to the invention, said syringe being represented in its injection phase. The parts or components of this embodiment which are similar to parts or components of the embodiments shown by FIGS. 1 and 2 will be designated by the same reference numbers. This syringe comprises an ampoule 1 having an ampoule body 2 and a neck 3 provided with an opening. The neck 3 is provided with an exterior rim 4. A capsule 5 is adapted to the neck 3 of ampoule 1. Capsule 5 is provided with projections 6 and with a needle holder tip 7.

In this embodiment, the rod element 8 of the stopper means comprising also a stopper body 9 is not integral with capsule 5 but is coupled to said capsule 5 by means of an annular groove 30 in which there engages a protruding annular rim 31 which is provided at the lower end of the rod element 8. Stopper body 9 and rod element are integral preferably made of a plastic material having resilient properties so that the stopper body can be brought into a compressed condition and into at least a partly expanded condition, and a sufficient stiffness so that the rod element remains rigid during the injection-/aspiration phase.

Stopper body 9 is provided with at least one transverse branch 16 communicating with an axial branch 18 centrally located through the rod element 8. Said stopper body is provided with an upper part 14 having a continuous annular surface 14A which is sealingly in direct contact with the neck inner wall during said closed storage phase, and with a lower part 15 having a continuous annular surface 15A which is sealingly in direct contact with the ampoule body inner walls during said opening injection/aspiration phase. In this embodiment upper part 15 is integral with the rod element 8.

Figure 4:
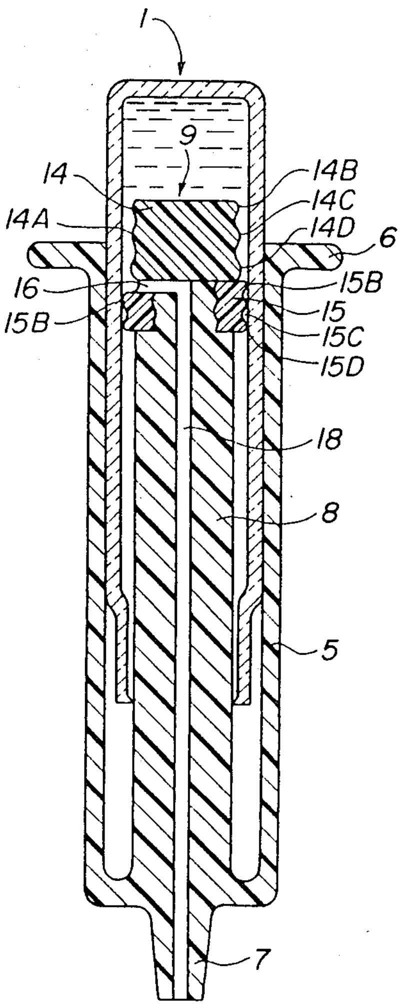
FIG. 4 is an axial section of another embodiment of the prefilled ampoule-syringe of the invention.

The embodiment of FIG. 4 differs from this of FIG. 3 in that the stopper body 9 is not integral with the rod element 8 and in that the upper part 14 and the lower part 15 of said stopper body are separate elements. The other components which are substantially similar to those of the embodiment of FIG. 3 are not described herein. Said continuous annular surface 14A of said upper part 14 is composed of several annular rims 14B, 14C, 14D which assume the sealing contact between said upper part 14 and the neck inner wall during said closed storage phase.

Said continuous annular surface 15A of said lower part 15 is composed of several annular rims 15B, 15C, 15D which assume the sealing contact between said lower part 15 and the ampoule body inner wall during said injection/aspiration phase.

In the embodiment shown by FIG. 4, the transverse branch 16 is located at the upper end of the lower part 15 and the rod element 8. Since upper and lower parts are disjoined, the transverse branch could be replaced by a space located between said parts, these parts being maintained in a spaced relationship, i.e. by a central upper tip of the rod element 8.

In all the above embodiments, the stopper body comprises an upper part 14 and a lower part 15. The upper part 14 is sealingly in direct contact with the neck inner walls during the closed storage phase and the lower part 15 is sealingly in direct contact with the ampoule body inner wall during the injection/aspiration phase. Therefore, the stopper body works like a stopper during said storage phase and like a piston during said injection phase. In order to permit flow of liquid to the transverse branch, the upper part must have outer dimensions which are smaller than the inner dimensions of the ampoule body and the lower part must have outer dimensions which are larger than the inner dimensions of the ampoule body.

In all these above described embodiments, the total length of the stopper means from the upper end of the upper part of said stopper body to the zone where the rod element is attached to the external capsule is at least equal to the total length of said ampoule body and said neck. Consequently, the whole volume of liquid can be substantially injected, since the stopper body can be pushed against the close end of the ampoule body.

We claim:

1. Prefilled ampoule-syringe containing a liquid medication and a gas and comprising an ampoule with a substantially rigid ampoule body having a single open end and a neck defining an inner wall located near said single open end, this neck having smaller transverse inner dimensions than said body, and an elastomeric stopper means associated with an external capsule, said stopper means being provided with an internal conduit having at least one transverse branch opening into a longitudinal branch for communication of the interior of the ampoule body with injection device holding tip, said stopper means being arranged for axial movement within said neck in a closed storage position and within said ampoule body in an open injection/aspiration position; in which said stopper means comprises a stopper body having an upper part located above said transverse branch and a lower part located below said transverse branch, and a rod element for attaching solidly at least said lower part of said stopper body to said external capsule, in which said upper part of said stopper body is provided with at least one continuous annular surface having larger transverse outer dimensions than the transverse inner dimensions of said ampoule neck so as to be in a compressed condition in said closed storage position sealingly engaged in direct contact with said substantially rigid inner wall of said neck in said closed storage position so as to prevent flow of liquid from the ampoule body to said transverse branch, said transverse branch terminating at the inner wall of said neck in this closed position and having at least partly smaller transverse outer dimensions than the transverse inner dimensions of said ampoule body, so as to be in at least a partly expanded condition in said open injection/aspiration position, and being at least partly disengaged from the inner wall of said ampoule body in said open injection-/aspiration position, said transverse branch being spaced from said inner wall in this open position so as to permit flow of liquid from the ampoule body to said transverse branch, in which said lower part of said stopper body is provided with at least one continuous annular surface having larger transverse outer dimensions than the transverse inner dimensions of said ampoule neck so as to be in a compressed condition in said closed storage position and being sealingly engaged in direct contact with said inner wall of said neck in said close position, and having also larger outer dimensions than the transverse inner dimensions of said ampoule body so as to remain in at least a partly compressed condition in said open injection/aspiration position, and being sealingly engaged in direct contact with the inner wall of said ampoule body in said open injection/aspiration position so as to prevent accidental flow of liquid from the transverse branch or ampoule body to the open end of the ampoule neck, and in which the total length of the stopper means from the upper end of the upper part of said stopper body to the zone where the rod element is attached to the external capsule is at least equal to the total axial length of said ampoule body and said neck.

2. Prefilled ampoule syringe according to claim 1, in which said upper part and said lower part of said stopper body are integral.

3. Prefilled ampoule syringe according to claim 1, in which said upper part and said lower part of said stopper body are separate elements.

4. Prefilled ampoule syringe according to claim 1, in which said lower part of said stopper body is integral with said rod element.

5. Prefilled ampoule syringe according to claim 1, in which said continuous annular surface of said upper part of said stopper body is provided with at least one ring-shaped rim.

6. Prefilled ampoule syringe according to claim 1, in which said continuous annular surface of said lower part of said stopper body is provided with at least one ring-shaped rim.

7. Prefilled ampoule syringe according to claim 1, in which said continuous annular surface of said lower part of said stopper body is provided with at least one ring-shaped strip or tongue.

* * * * *